United States Patent [19]

Fixot

[11] 4,335,673
[45] Jun. 22, 1982

[54] APPARATUS FOR THE COLORING OF SLIDES

[76] Inventor: Marcel J. Fixot, La Basse Chevrie, 35590 L'Hermitage, France

[21] Appl. No.: 38,636

[22] Filed: May 14, 1979

[30] Foreign Application Priority Data

May 17, 1978 [FR] France ............................ 78 15167

[51] Int. Cl.³ .............................................. B05C 11/08
[52] U.S. Cl. ..................................... 118/52; 118/401
[58] Field of Search ............... 118/401, 52, 54, 56; 427/4, 2

[56] References Cited

U.S. PATENT DOCUMENTS

| | | | |
|---|---|---|---|
| 2,386,591 | 10/1945 | Campbell | 118/52 |
| 3,352,280 | 11/1967 | Hughes et al. | 118/326 X |
| 3,667,896 | 6/1972 | McCormick et al. | 427/2 X |
| 3,985,096 | 10/1976 | Guimbretiere | 118/58 |
| 4,199,613 | 4/1980 | Johnson | 427/4 X |

FOREIGN PATENT DOCUMENTS 1166088 10/1969 United Kingdom .

*Primary Examiner*—John P. McIntosh
*Attorney, Agent, or Firm*—Laff, Whitesel, Conte & Saret

[57] ABSTRACT

In a slide coloring apparatus for smear preparations, the slides are placed into small cavities, at a distance from the cavity bottom such that the reagents provided for the coloring are spread on each slide by capillarity.

The cavities are provided in the peripheral zone of a circular tray which is capable of rotating at a more or less high speed. The cavities are open toward the edge of the tray, and are separated by swellings. Each reagent is poured into the central zone of the tray and it flows into the cavities by centrifugal action, with the tray rotating at a low speed. After the time needed for each reaction, the reagent is evacuated through the edge of the tray, by centrifugal action, with the tray then rotating at high speed.

The invention is especially usable for coloring blood smear preparations.

6 Claims, 3 Drawing Figures

APPARATUS FOR THE COLORING OF SLIDES

The present invention relates to an apparatus for the automatic coloring of slides serving for the preparation of smear preparations and, more especially, of blood smear preparations.

The making of blood smear preparations comprises a spreading of one drop of blood on a glass slide, then there is a coloring and fixing of the thin pellicle by means of suitable liquid reagents. In a well known preparation, in a first step, a few drops of a May Grunwald reagent are poured on the slide; then, in a second step, water is added in equal volume. The mixture is spread over the slide to impregnate the thin pellicle of blood in a homogenous manner. Finally, in a third step, there is poured over the slide a quantity of diluted Giemsa reagent, in a volume sufficient to cover it entirely. That reagent has to be prepared immediately prior to its being used. To complete the preparation, the slide must be completely dried.

For a long time, in most analysis laboratories, those various operations were generally carried out by hand. Besides, they presented quite a number of difficulties. In the first place, the mixture formed by the water and the May Grunwald reagent has a surface tension such that it spreads poorly, and shows a tendency to remain in the form of drops. It is therefore necessary to slant the slide far enough to cause the drops to roll down, but not far enough to fall off the slide. Moreover, between the various operations of addition, there must elapse very definite periods of time which are sometimes difficult to respect, especially when a large number of slides are being treated. Finally, as already indicated, the Giemsa reagent must be prepared at the last moment. The result of the above was that the manual preparation of the slides was not always perfect. It was especially difficult to obtain, and for obvious reasons related to human inaccuracies, homogenous colorings which afterwards help the examination of the slides under the microscope.

In order to avoid the above-indicated drawbacks, various apparatus with automatic operations have been suggested. Thus, there is a known automatic coloring apparatus in which the slides are horizontally translated on a plate while maintaining a capilllary space to introduce the reagents. Such an apparatus, for example, is described in U.S. Pat. No. 3,667,896. That apparatus, however, does not make it possible to use varied reagents, such as those indicated above, so that the final colorings are different from those to which the operators are used.

There are also apparatus in which the coloring operations are carried out by a dipping into the reagents. Those apparatus present two drawbacks. In the course of treatment of a series of slides, there is a progressive reduction in strength of the coloring agent baths, this making the colorings uniform. During the dipping operation, the two opposite side faces of the slide are colored, thus making it necessary to clean the back of the slide prior to its examination under microscope.

There is still another known automatic coloring apparatus, which is described in French Pat. No. 2,263,502, in which is an endless belt conveyor fitted with elastic vacuum cups to which the back of the slides adheres during treatment. A loading station comprises means to apply each slide to be treated on a vacuum cup, with a given pressure, and an unloading station comprises means to deform each vacuum cup so that it will release the slide it carries. The trajectory of the conveyor comprises an upper horizontal part above which are arranged the addition distributors. A lower horizontal part comprises a drying zone, an unloading zone and a loading zone. Means are provided for in the upper horizontal part to cause the slides to pitch and to roll in order to facilitate the spreading of the reagents. That apparatus has as its advantages, a high level of automation. The fact that the surface of the slide opposite that on which the smear preparation is spread, is located inside the perimeter of the vacuum cup masks it so that it remains perfectly clean. This facilitates and renders a more accurate the examination under the microscope. On the other hand, relatively complex means are required to ensure a good spreading of the reagents over the active face of the slide.

One object of the present invention is to provide for an apparatus which presents the major advantages of the above-indicated apparatuses, without presenting their drawbacks.

Another object of the invention is to provide for an extremely simple apparatus the structure.

Another object of the present invention is to provide for an apparatus in which the spreading of the reagents is achieved by capillarity.

Another object of the invention is to provide for an apparatus which makes it possible to treat a relatively large number of slides at the same time and in parallel.

According to a characteristic of the invention, a slide coloring apparatus enables the slides to be placed into cavities, at a distance from the bottom of the cavities such that the reagents needed for the coloring are spread under each slide by capillarity action. The cavities are provided in the peripheral zone of a circular plate which may rotate at various speeds, the cavities being open toward the edge of the plate and separated from one another by swellings.

Other characteristics will appear more clearly upon a reading of the following description of one example of execution, the description being given with reference to the attached drawing in which.

Figure 1:
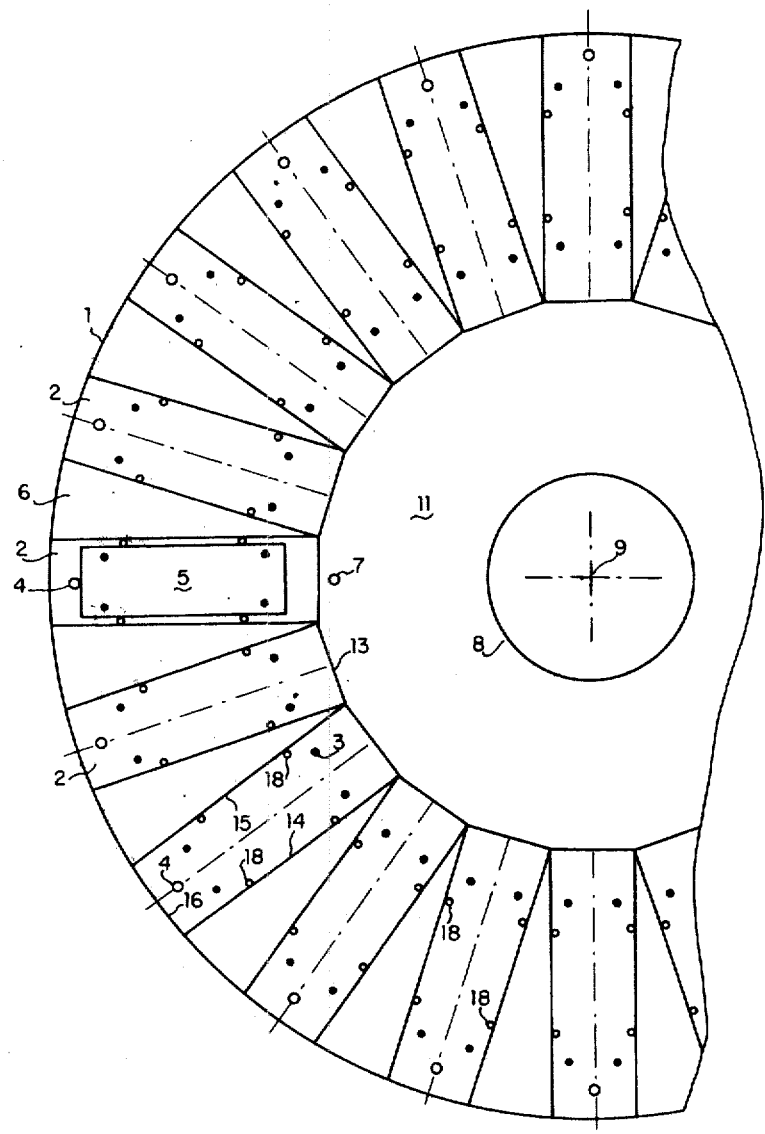
FIG. 1 is a schematic and partial view, from the top, of an apparatus according to the present invention.
Figure 2:
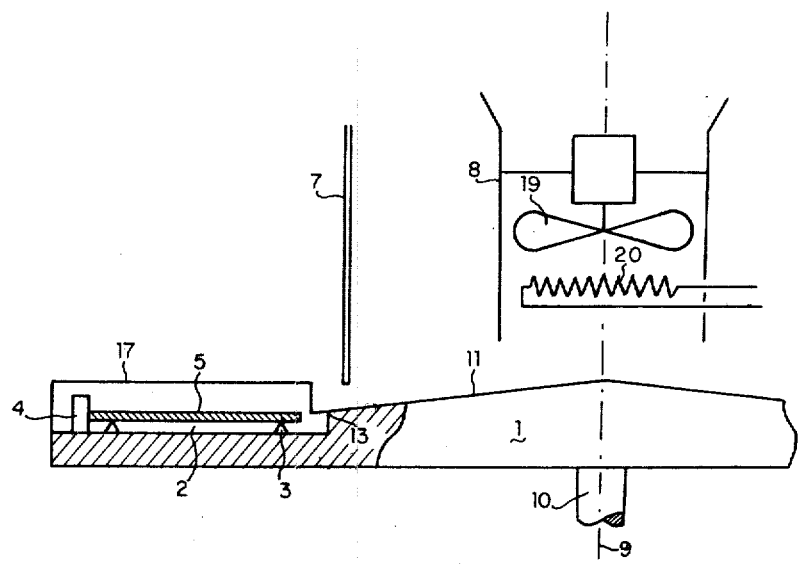
FIG. 2 is a schematic and partial section view of the plate in FIG. 1, and of other components of the apparatus according to the invention.

As seen in FIGS. 1 and 2, the coloring apparatus comprises a plate 1, which can be made to rotate around an axis 9 and which is set at the end of a shaft 10. Plate 1 comprises, at its periphery, a series of cavities 2 generally rectangular in shape, separated by swellings 6. The central zone of plate 1 presents a slightly cone-shaped surface 11. The opening of the cone is at the point which is on shaft 9, being downward directed. The base surface 12 of the cavities 2 is practically horizontal and, preferably it is located at a level which is lower than the edges 13 of the cone-shaped surface 11.

Thus, each cavity 2 has the general appearance of a rectangular chamber, the two lateral walls 14 and 15 of which are formed by swellings 6, the central wall of which is formed by edge 13, and which is open toward the outside, at the edge 16 of plate 1.

The upper surface 17 of each swelling 6 is at a level which is higher than the level of the cone-shaped surface 11, at least in the neighborhood of of edge 13. As shown in FIG. 1, each swelling 6 is triangular in shape, with its point turned toward the plate's center.

The lower surface 12 of each cavity 2 presents three or four points 3, the point of which is upwardly directed. The cavities in the example of the described embodiment, each comprising four points 3. Moreover, on the radial axis of each cavity 2, there is a lug piece 4 while, along the lateral edges of each cavity 2, there are lug pieces 18. Also on the radial axis of each cavity 2 it is possible to provide, on the inside edge 13, a lug piece similar to lug piece 4. The lug pieces are separated by distances which are approximately equal, with the necessary play, to the length and width of a slide 5 to be colored.

It is well known that the slides to be colored have practically standardized sizes. It is therefore easy to define the spacing between lug pieces 18.

Above surface 11, close to edge 13, there is an open duct 7 through which one or several reagent or reagents can be poured over surface 11. Instead of a single duct 7, represented in order to illustrate the apparatus, it is obviously possible to provide for as many ducts as there are different reagents which must be used during the coloring operations. Above the central part of zone 11, there is also an air intake duct 8, which may be hot air. As an example, in FIG. 2 there has been represented duct 8 containing a fan 19 and a heating resistance 20.

Figure 3:
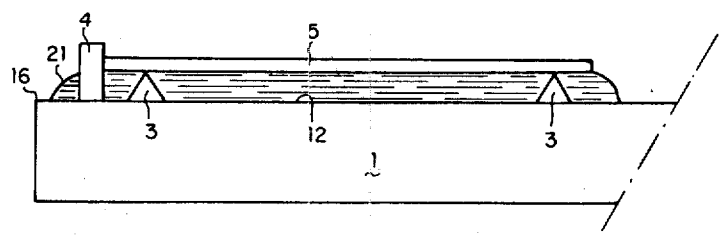
FIG. 3 is a schematic section view, in larger scale, of a slide placed on the apparatus, according to the invention, making it possible to illustrate the operation of the apparatus.

There will now be described the operation of the apparatus according to the invention. Disk 1 being at rest, the smear preparation slides 5 are placed in cavities 2, between lug pieces 4 and 18. The side of the slide with the smear preparation is directed toward surface 12. As shown in FIG. 2, it is possible to see that slide 5 is appreciably above level 17 of sidewall 6. As shown in FIG. 3, slides 5 rest on the tips of points 3 which define between the surface of the smear preparation and surface 12 a relatively thin space interval. Lug pieces 4 and 18 limit any lateral displacement of slide 5.

The slides to be colored being thus placed inside cavities 2, plate 1 is made to rotate slowly, at a low speed of a few rotations per minute. The reagent is made to arrive through duct 7, the first one being a fixing agent. The liquid poured through duct 7 over surface 11 runs down into cavities 2 by gravity and under the action of the centrifugal force. The height of points 3 is such that the space interval between 5 and 12 enables the spreading by capillarity of the show liquid under slide 5, but it prevents, at the speed of rotation under consideration, the liquid from escaping through edge 16, forcing it to form a flange 21.

It must be noted that lug pieces 18 which prevent any contact between slide 5 and an edge 14 or 15 prevent the liquid from going back up above the slide. That is the main function of lug pieces 18.

After a given period of time, the plate possibly continues to rotate at low speed or is even stopped once it has been observed or estimated that the liquid has become well spread under the slides. Plate 1 is thereafter made to rotate at high speed, at a few hundreds of rotations per minute, for example, this resulting in destroying the liquid flange 21 and in driving it away above edge 16, under the centrifugal action, the liquid being dispelled from the space between 5 and 12.

The above-described operations can be repeated, that is to say the spreading of the liquid at low speed of rotation, then, after a given period of time, evacuation of the liquid at high speed of rotation, for various products.

After those operations, plate 1 still is made to rotate at high speed, and fan 19 and resistance 20 are made to operate. The hot air, supplied through duct 8, is directed over surface 11 and, partially at least, it runs between the slides 5 and the bottoms 12 of the cavities, thus drying them rapidly. In practice, it has been possible to observe that drying was complete and rapid. Indeed, the air running under the slides drives along the drops which might have remained after centrifugation of the liquid, and it does not dry them on the slide, a situation which would leave drying rings which are a classical problem and which hinder an observation under the microscope.

In practice, instead of providing for a single drying operation at the end, it is possible to provide for as many drying operations as desirable between the applications of liquid reagents.

Upon reading the preceding description, it clearly can be seen that the apparatus according to the invention preserves the advantages offered by the already existing apparatuses, and especially the fact that the upper face of slide 5 is left dry, without any coloration. It is possible to use conventional reagents. Especially, it is possible to use reagents and then to proceed to washings with water. Indeed, a duct 7 may be reserved for water.

In addition, the volume of liquid retained under the slide being definite, as a result of the geometry of the cavity and of the capillarity effect, it is possible to avoid sending an excess of liquid through duct 7, as is done in the known apparatuses. Thus, only very little reagent is used. Finally, cleanings between each operation are highly efficient as they are the evacuation forces created by the high speed of rotation of plate 1.

As an indication, plate 1 may have a diameter of the order of 40 to 50 centimeters, thus making it possible to treat, in a single operation, approximately 30 slides, a fact which is important. The washing and drying operations are very short ones. The coloring operations can be executed rapidly. The time periods required for the reaction of the reagents, however, are not compressible. In this way, the apparatus makes it possible to treat a large number of slides, and the time required for a coloring operation is almost at a minimum.

It must be understood that lug pieces 18 only serve to separate slide 5 from the edges of the cavity, and must have only a very small diameter so that no drop of water could become caught behind them.

Points 3 and lug pieces 4 and 18 are, as much as possible, planned to come from molding at the same time that the remainder of the plate is molded. But, the lug pieces can also be separately driven into the cavities, if necessary.

I claim:

1. Apparatus for coloring slides having smear preparations thereon, said apparatus comprising rotatable means having a plurality of shallow recesses circumferentially distributed around the periphery thereof, said recesses being separated from each other by sidewall swellings and being open at the periphery of said rotatable means, means in each of said cavities for supporting a slide in a position which is elevated above the bottoms of said recesses far enough to enable a liquid coloring reagent to spread under said slide responsive to capillary action, means for rotating said rotatable means at either a high speed or a low speed RPM, and means for selectively introducing a reagent into each of said recesses, the reagent being introduced from the central area of said rotating means, whereby said reagent may be distributed under a slide by low speed centrifugal forces and expelled from under said slide by high speed centrifugal forces.

2. The apparatus for coloring slides according to claim 1, in which said elevating means are point means in each of said recesses on which a slide to be treated rests, the height of said point means defining a space interval under the slide in which the reagent spreads.

3. The apparatus for coloring slides according to claim 1 or 2, in which longitudinal positions of each slide in its recess are limited by lug pieces.

4. The apparatus for coloring slides, according to claim 3, characterized in that each slide is separated from the side walls of its recess by lug pieces of very small diameter.

5. The apparatus for coloring slides according to claim 3 wherein a central zone of the rotatable means is slightly cone-shaped to cause liquid to run down into said recesses.

6. The apparatus for coloring slides according claim 5 wherein the central zone of the plate includes a hot air intake means which operates for the drying operations.

* * * * *